United States Patent [19]

Ohwaki et al.

[11] Patent Number: 5,468,633
[45] Date of Patent: Nov. 21, 1995

[54] HUMAN ENDOTHELIN CONVERTING ENZYME OBTAINED FROM BLOOD OR PLACENTA

[75] Inventors: Tatsuya Ohwaki; Hiroshi Sakai, both of Ohimachi, Japan

[73] Assignee: Nisshin Flour Milling Co., Ltd., Tokyo, Japan

[21] Appl. No.: 288,395

[22] Filed: Aug. 10, 1994

[30] Foreign Application Priority Data

Aug. 13, 1993 [JP] Japan .................... 5-201368

[51] Int. Cl.$^6$ .............. C12N 9/48; C12N 9/50; C12N 9/64
[52] U.S. Cl. ............... 435/212; 435/219; 435/226
[58] Field of Search ................... 435/212, 219, 435/226

[56] References Cited

FOREIGN PATENT DOCUMENTS 0545344  6/1993  European Pat. Off. .
92/13944  8/1992  WIPO .

OTHER PUBLICATIONS

Ohwaki et al. (1993) *Atherosclerosis*, 102(2) 227–228.
Ohnaka et al. (1993) *J. Biol. Chem.* 268(35) 26759–26766.
Ikura et al. (1994) *Biochem. Biophys. Res. Chem.*, 203(3), 1417–1422.
Okada et al. (1990) *Biochem. Biophys. Res. Comm.*, 171(3), 1192–1198.
Sawamura et al. (1990) *Biochem Biophys, Res. Comm.*, 172(2), 883–889.
Sawamura et al. (1993) *Biochem. Biophys. Acta*, 1161, 295–302.
Sakai et al. (19 Oct. 1993) JP 05, 268, 956 in *Chem. Abst.* 120, 395, Abst #72,415.
Sekai et al. (31, Jul. 1992) JP-04,210,593, in *Chem. Abst.* 117, Abst #229,115.
Knap et al. (1993) *J. Cardiovasc. Pharmacol.*, 22(Suppl. 8), S90–S93, in *Chem. Abst,* 120(17), Abst. #73, 979.
Shinmi et al. (1993) *J. Cardiovasc. Pharmacol.*, 22(Suppl. 8), S61–S64, in *Chem. Abst.*, 120(17), Abst. #211, 159.
Wildinson et al. (1993) *Biochem. Soc. Trans.*, 21(3), 276S.
Nature, vol. 352, 411–415, M. Yanagisawa, et al., Mar. 31, 1988, *A Novel Potent Vasoconstrictor Vascular Endothelial Cells*.
Biochem. and Biophys. Res. Commun., vol. 171, No. 3, 1192–1198 (Sep. 28, 1990) *Conversion of Big Endothelin–1 by Membrane–Bound Metalloendopeptidase in Cultured Bovide Endothelial Cells* By Kenji Okada, et al.
Biochem. and Biophys. Res. Commun., vol. 168, No. 3, 1230–1236 (May 16, 1990) *Purification and Characterization of Putative Endthelin Converting Enzyme in Bovine Adrenal Medulla: Evidence for a Cathepsin D–Like Enzyme* By Tatsuya Sawamura, et al.
FEBS Letters, vol. 320, No. 2, pp. 165–168 (1993) *Endothelin–Converting Enzyme Activity in Human Serum Lipoprotein Fraction* By Tatsuya Ohwaki, et al.
JAMA, vol. 264, No. 22, p. 2868, Dec. 12, 1990, K. Kanno, et a., *Endothelin–1 and Vasculitis*.
N. Engl. J. Med., 325, No. 14, pp. 997–1001 (Oct. 3, 1991) *Circulating and Tissue Endothelin Immunoreactivity in Advanced Atherosclerosis* By Amir Lerman, M.D., et al.

(List continued on next page.)

Primary Examiner—David M. Naff
Assistant Examiner—Jon P. Weber
Attorney, Agent, or Firm—Oblon, Spivak, McClelland, Maier & Neustadt

[57] ABSTRACT

A human endothelin converting enzyme (ECE) has been isolated from blood and placenta. The enzyme has the activity of converting big endothelin-1, -2, or -3 to endothelin-1, -2, or -3 respectively. The enzyme has a mass of about $5.4 \times 10^5$ by gel filtration, a pH optimum of 6.5 to 7.5, and a hydrated density of less than 1.210. The enzyme is inhibited by EDTA, phosphoramidon, thiorphan, chymostatin and phenylmethylsulfonylfluoride (PMSF). The enzyme is precipitated by 0.65% dextran sulfate or 0.2M manganese chloride. The enzyme can be inactivated by oxidation by copper ion.

2 Claims, 3 Drawing Sheets

OTHER PUBLICATIONS

Atherosclerosis 89, 239–246 (1991) *Increased Plasma Immunoreactive Endothelin–1 Concentration in Hypercholesterolemic Rats* By Takeshi Horio, et al.

Chemical Abstracts 117(3): 22489c, Jul. 20, 1992; JP 04–79883, Mar. 13, 1992.

Biochem. and Biophys. Res. Commun., vol. 176, No. 2, 860–865, Apr. 30, 1991, *Phosphoramidon–Sensitive Endothelin–Converting Enzyme in the Cytosol of Cultured Bovine Endothelial Cells* By Junji Takada, et al.

Biochem. and Biophys. Res. Commun., vol. 174, No. 2, 446–451 Jan. 31, 1991, *Endothelin Convering Enzyme of Bovine Carotid Artery Smooth Muscles* By Yoshio Hioki, et al.

FASEB Journal, vol. 5, No. 5, A1417 (1991).

Proc. Natl. Acad. Sci. USA, vol. 89, 8606–8610, Sep. 1992, *The Endothelin–Converting Enzyme from Human Unbilical Vein is a Membrane–Bound Metalloprotease Similar to that from Bovine Aortic Endothelial Cells* By Kyunghye Ahn, et al.

FASEB Journal, vol. 6, 2653–2659, Jun. 1992, *Endothelin–Converting Enzymes* By Terry J. Opgenorth, et al.

1. THYROGLOBULIN (M.W. 670000)
2. γ-GLOBULIN (M.W. 158000)
3. EGG ALBUMIN (M.W. 44000)
4. MYOGLOBIN (M.W. 17000)

HUMAN ENDOTHELIN CONVERTING ENZYME OBTAINED FROM BLOOD OR PLACENTA

BACKGROUND OF THE INVENTION

This invention relates to endothelin converting enzymes of human blood origin or human cell origin having the activity of converting big endothelin to endothelin and also to a process for preparing endothelin converting enzymes from human blood and human cells by extraction and purification.

Endothelin is an endothelial cell-derived vascular smooth muscle constricting factor discovered by Yanagisawa et al. in 1988, the presence of which has been identified in porcine, bovine and human or the like [M. Yanagisawa et al., Nature, Vol. 332, 411 (1988)].

Endothelin includes three types of isopeptides which are named endothelin-1, endothelin-2 and endothelin-3, respectively. Of these isopeptides, endothelin-1 has been confirmed to show the highest activity in human body. Endothelin, having strong and lasting action of constricting vascular smooth muscle cell and trachea, induces hypertension and constriction of respiratory tract and also induces at a high concentration (about 1–50 pmol/ml in blood level) ischemic cerebral and cardiac diseases such as cerebral apoplexy, stenocardia, myocardial infarction, cardiac incompetence and arrhythmia, nephropathy such as nephritis, circulatory failure of lung, liver and intestine, and asthma, thus sometimes bringing animals to the death.

Endothelin-1 is a 21-amino acid peptide which is produced by cleaving its precursor peptide, big endothelin-1 (SEQ IQ NO:1) of the formula:

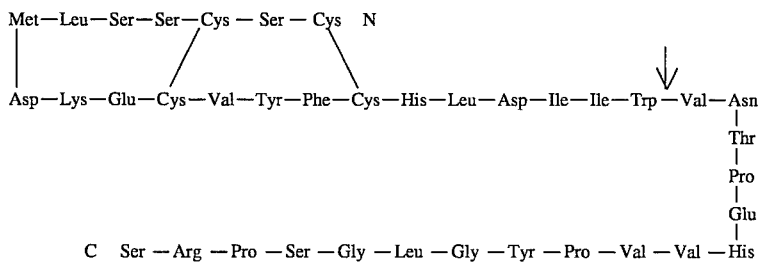

with the endothelin converting enzyme at the bond between the tryptophane residue at the 21st position from the N-terminus and the valine residue at the 22nd position from the N-terminus (shown by the downward arrow). This hydrolysis process is considered to be essential for production of endothelin-1 in vivo. Endothelin converting enzymes of bovine origin are those derived from cultured bovine endothelial cells or the like [K. Okada et al., Biochemical and Biophysical Research Communications, 171, No. 3, 1192 (1990)] and those derived from bovine adrenal medulla [T. Sawamura et al., Biochemical and Biophysical Research Communications, 168, No. 3, 1230 (1990)]. Regarding endothelin converting enzymes of human origin, WO 92/13944 discloses those prepared from human lung.

Endothelin having remarkable physiological activities as described above is produced enzymatically from its precursor i.e. big endothelin (SEQ ID NO:1). Therefore, the elucidation of the endothelin converting enzyme will provide a means for inhibiting the production of endothelin in vivo. In addition, this endothelin converting enzyme is expected to provide a useful reagent for analyzing the mechanism of vasoconstriction in vivo and for studying various diseases induced by endothelin.

Further, the elucidation of the endothelin converting enzyme (ECE) will provide an effective tool for searching and developing an ECE-inhibitor which would be clinically useful in the prophylaxis and treatment of various diseases (hyperendothelinemia) induced by hypersecretion of endothelin, such as hypertension, constriction of trachea, ischemic brain diseases and heart diseases, nephropathy, circulation failure of various organs (e.g., liver, lung, intestine, etc.), and asthma or the like.

Many reports were made on the relationship between atherosclerosis and endothelin. Atherosclerosis is a pathologic condition progressing by the abnormal proliferation of vascular smooth muscle cells. Further, Komuro, I. et al by FEBS Lett., 238, 249–252 (1988) have reported that ET-1 functions as a strong growth factor of vascular smooth muscle cells. Kanno, K. et al by JAMA, 264, 2868 (1990) have reported that patients with atherosclerosis exhibit significantly increased plasma levels of ET-1 as compared with healthy humans. Lerman, A. et al by N. Engl. J. Med. 325, 997–1001 (1991) have reported that plasma ET-1 concentrations show positive correlation with the extent of atherosclerotic vascular lesions.

Regarding the correlation between hyperlipemia which is the most common risk factor for atherosclerosis and endothelin, Horio, T. et al by Atherosclerosis, 89 (1991), 239–246 have reported that plasma ET-1 concentration in hypercholesterolemic rats increases significantly as compared with healthy rats and also that there is positive correlation between plasma total cholesterol levels and plasma ET-1 concentration in hypercholesterolemic rats.

From the above reports, it is considered that elevated plasma ET-1 level by hyperlipemia functions as a growth factor of vascular smooth muscle cells which contributes to the progress of atherosclerosis.

However, it remains unknown why plasma ET-1 concentration will increase by hyperlipemia.

SUMMARY OF THE INVENTION

As a result of intensive investigations to prepare endothelin converting enzyme from human origin being easily available, we have found that an endothelin converting enzyme having the properties like apolipoprotein B-100 exists in the lipoprotein fraction of human blood and human cells.

Since the ECE activity of the present invention is present in a lipoprotein fraction, the mechanism on elevated plasma ET-1 concentration in hyperlipemia can be explained without contradiction. Thus, the present invention contributes largely to the explanation of such mechanism. By the investigation of inhibitors against the endothelin converting enzyme of the present invention contained in the lipoprotein fraction, there can be provided a means for preventing an increase in plasma ET-1 concentration caused by hyperlipemia, eventually the development of atherosclerosis.

This invention provides an endothelin converting enzyme of human cell origin and human blood origin, which has the following (1)–(8) properties.

(1) Action: being capable of converting big endothelin to endothelin;

(2) Substrate specificity: acting on big endothelin-1, big endothelin-2, or big endothelin-3;

(3) Optimum pH: pH 6.5–7.5;

(4) Molecular weight: about $5.4 \times 10^5$ as measured on gel-filtration using a column of crosslinked agarose gel bead (exclusion limit $5 \times 10^6$ Daltons);

(5) Inhibitors: inhibited by ethylenediaminetetraacetate (EDTA), phosphoramidon, thiorphan, phenylmethanesulfonyl fluoride (PMSF), and chymostatin;

(6) Hydrated density: not greater than about 1.210 g/ml;

(7) Formation of precipitate: precipitation by adding 0.65% dextran sulfate (M.W. 500,000) and 0.2M manganese chloride;

(8) Influence of oxidation: inactivated by oxidation by copper ion.

DETAILED DESCRIPTION OF THE INVENTION

Figure 1:
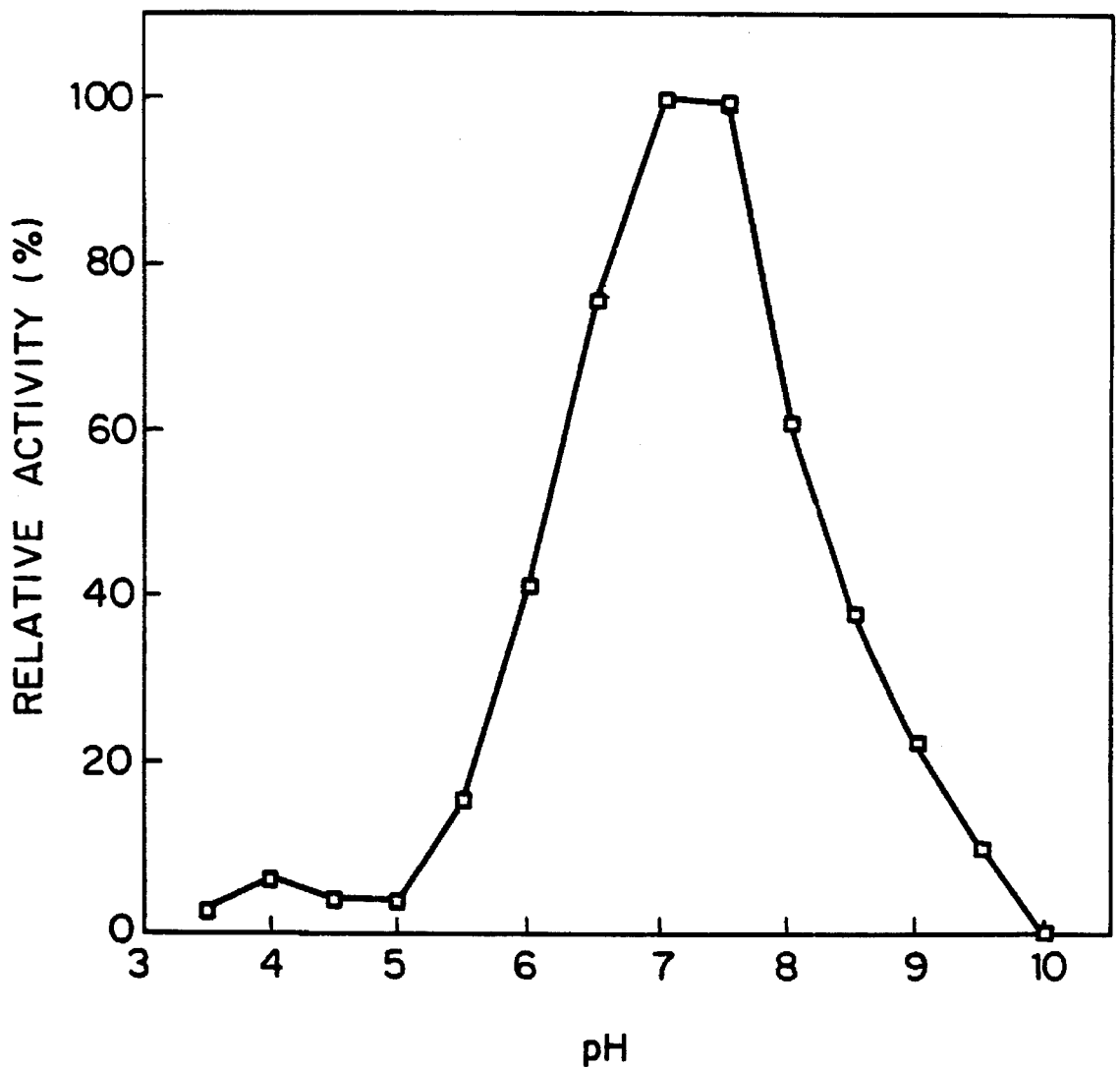
FIG. 1 is a graph showing the test results at optimum pH for the endothelin converting enzyme obtained in Example 1.

The endothelin converting enzyme of the invention is like apolipoprotein B-100 prepared by extracting from human blood, the cells of human organs or tissues such as liver, small intestine, placenta or their cultured cells. Human blood and placenta are advantageously used because of their easy availability. However, other organs and tissues than blood and placenta may also be used for the extraction with sacrificing availability.

The endothelin converting enzyme of the invention shows somewhat resemblance in properties and behavior to apolipoprotein B-100 which is one of the lipoprotein-constructing proteins. However, apolipoprotein B-100 is generally insoluble in water, whereas the present endothelin converting enzyme has different properties in respect of water-solubility or the like. In this regard, the endothelin converting enzyme of the invention is new protein being different from apolipoprotein B-100.

The endothelin converting enzyme of the invention can be prepared from human blood and the cells of human organs such as liver, small intestine, placenta and human tissues or their cultured cells.

For example, in the case of using human blood as original material, the present endothelin converting enzyme can be prepared by adding salts to the serum or plasma obtained from the human after one night fasting, adjusting the density to about 1.210 g/ml, centrifuging the solution at 100,000–200,000 g for 20–40 hours and subjecting a fraction floating to the surface to a column of gel filtration chromatography. More particularly, the endothelin converting enzyme can be prepared by the following procedure. Serum or plasma is separated from the blood of the human after one night fasting, and a salt such as potassium bromide is added to adjust the density of serum to about 1.210 g/ml. After adjusting the pH to about 7.0, the solution is centrifuged at 4°–25° C., preferably 4°–15° C. at 100,000–200,000 g for 20–40 hours. A fraction floating to the surface is collected. After dialyzing the fraction overnight, the dialysate is concentrated to its appropriate volume and subjected to a column of gel filtration chromatography to collect a fraction having a molecular weight of about 540,000 as the endothelin converting enzyme of the invention.

The column of gel filtration chromatography which can be employed in the invention includes crosslinked agarose gel bead (exclusion limit $5 \times 10^6$ Daltons), e.g., Bio-Gel A-5m available from Bio-Rad Laboratories (Richmond, Va., USA), Sepharose 6B available from Pharmacia AB (Uppsala, Sweden) or the like.

Alternatively, in the case of using human organs or tissues as original material, the present endothelin converting enzyme can be prepared by homogenizing human organs, human tissues, or their cultured cells, separating a supernatant from the resultant homogenate, adding salts to the supernatant to adjust the density to about 1.210 g/ml, centrifuging supernatant in a similar manner as performed for blood or plasma to collect a floating fraction and further subjecting the fraction to a column of gel filtration chromatography. More particularly, the endothelin converting enzyme can be prepared by the following procedure. Organs or tissues are cut into fine pieces, a suitable amount of buffer such as a 25 mM HEPES-0.25M sucrose buffer (pH 7.4) is added and the mixture is homogenized at a lower temperature in a commonly employed homogenizer such as a Potter-type homogenizer. The resultant homogenate is centrifuged to collect a supernatant. The supernatant of organs or tissues collected by the foregoing procedure is further centrifuged at 50,000–100,000 g to recover another supernatant by which there is obtained a cytoplasmatic fraction of the organs or tissues. The cytoplasmatic fraction is dialyzed against an aqueous sodium chloride solution, the density of which has been adjusted to about 1.006 g/ml or alternatively is subjected to desalting column equilibrated with an aqueous sodium chloride solution, the density of which has been adjusted to about 1.006 g/ml, followed by elution with the same aqueous sodium chloride solution, thus replacing the solvent in the cytoplasmatic fraction with an aqueous sodium chloride solution having the density of about 1.006 g/ml. After adjusting the density of the cytoplasmatic fraction to about 1.210 g/ml in a similar manner as performed for serum or plasma, the fraction is subjected to centrifugation and gel filtration column chromatography to obtain the endothelin converting enzyme of the invention.

Activity of the endothelin converting enzyme of the invention is expressed in terms of the titer which is measured in the following manner.

(1) Determination of enzyme activity

15 µl of a 20 nmol/ml big endothelin-1 solution was added to 0.3 ml of an enzyme solution (10 mM tris-hydrochloric acid-0.15M sodium chloride buffer; pH 7.0), and the mixture was reacted at 37° C. for 6 hours. After completion of the reaction, 6 µl of a 0.1M EDTA solution was added to terminate the reaction.

Subsequently, the resultant endothelin-1 was assayed according to a sandwich enzyme immunoassay (EIA) method. An enzymatic activity of converting 1 pmol of big endothelin-1 to endothelin-1 per hour under the above-described reaction conditions is termed 1 U (unit).

(2) Sandwich-EIA method

A sample and an endothelin standard solution of a predetermined concentration were respectively applied to a 96-hole microplate on which anti-endothelin monoclonal antibody had been immobilized to thereby cause the reaction. After washing the microplate, peroxidase-labeled anti-endothelin polyclonal antibody was added to thereby cause the reaction. After washing the microplate, activity of bound peroxidase was assayed. Endothelin-1 in the sample was assayed based on the calibration curve drawn by using endothelin standard solutions having a predetermined concentration of endothelin.

The endothelin converting enzyme of the invention has the following enzymatic and chemical properties.

(a) Substrate specificity

15 μl of a 20 nmol/ml of big endothelin-1 or big endothelin-2 or big endothelin-3 solution was added to 0.3 ml of the solution of the endothelin converting enzyme of the invention (10 mM tris-hydrochloric acid-0.15M sodium hydrochloride buffer, pH 7.0), and the respective mixture was reacted at 37° C. for 6 hours. After completion of the reaction, 6 μl of a 0.1M EDTA solution was added to terminate the reaction. Whether or not to produce endothelin-1 or endothelin-2 or endothelin-3 was examined according to the sandwich-EIA method specific to endothelin-1, endothelin-2 or endothelin-3. As a result, the endothelin converting enzyme of the present invention was found to produce endothelin-1 from big endothelin-1, endothelin-2 from big endothelin-2 and endothelin-3 from big endothelin-3.

(b) Optimum pH

Optimum pH of the endothelin converting enzyme of the invention was measured by adding the endothelin converting enzyme to a solution of big endothelin-1 in 50 mM each buffer with varying pH levels, and conducting the reaction at 37° C. The following buffer solutions were used.

pH 3.6–6.0 Citric acid-sodium citrate buffer pH 6.0–7.0 PIPES-sodium hydroxide buffer pH 7.0–9.0 Tris-hydrochloric acid buffer pH 9.0–10.0 Sodium carbonate-sodium hydroxide buffer Measurement reveals that the endothelin converting enzyme of the present invention exhibits the highest activity in a range of pH 6.5–7.5 as shown in FIG. 1.

(c) Inhibitors

The enzyme of the invention was tested for the effects of various inhibitors against the activity of converting big endothelin-1 to endothelin-1.

The enzyme was incubated in 0.3 ml of a reaction solution (10 mM tris-hydrochloric acid-0.15M sodium chloride buffer; pH 7.0) containing various inhibitors at 37° C. for 30 minutes, and the residual enzymatic activity was measured in the above-described manner. Residual activities in the presence of various inhibitors are shown in Table 1 as relative activity taking the activity of untreated enzyme as 100.

TABLE 1

| Inhibitor | Concentration (mM) | Relative Activity (%) |
| --- | --- | --- |
| Control | — | 100 |
| Ethylenediaminetetraacetate (EDTA) | 1 | 0 |
| Phosphoramidon | 0.1 | 0 |
| Phenylmethanesulfonyl fluoride | 1 | 7 |
| Chymostatin | 0.01 | 20 |
| Thiorphan | 0.1 | 0 |

(d) Molecular weight

Figure 2:
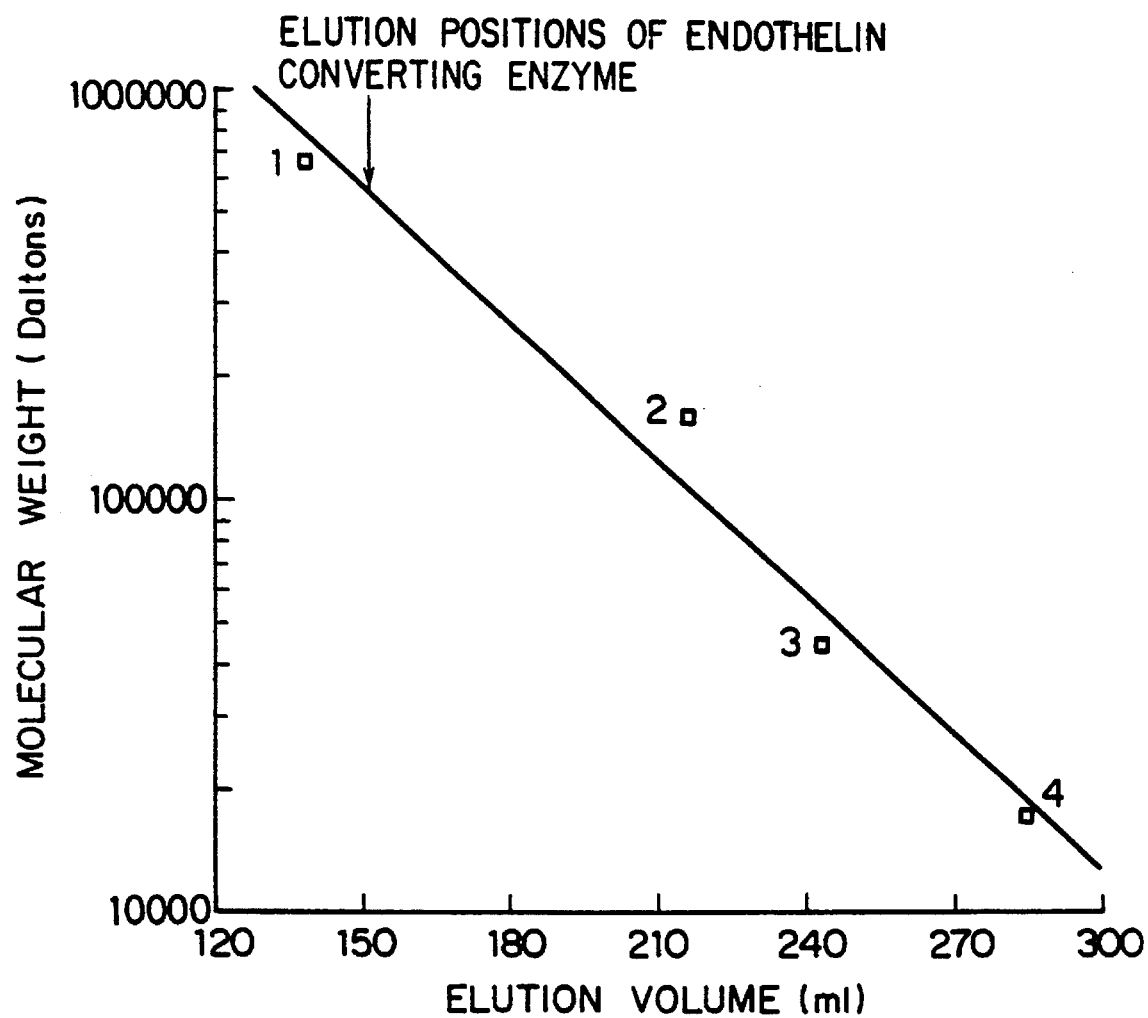
FIG. 2 is a graph showing a standard curve for measuring the molecular weight by gel filtration using a column of Bio-Gel A 5m and the test results for determing the molecular weight of endothelin converting enzyme obtained in Example 1.

Globular proteins of known molecular weights (thyroglobulin M.W. 670,000, γ-globulin M.W. 158,000, egg albumin M.W. 44,000, myoglobin M.W. 17,000) were separated and fractionated by a gel filtration column chromatography on a column of crosslinked agarose gel bead (exclusion limit $5 \times 10^6$ Daltons), Bio-Gel A-5m available from Bio-Rad Laboratories, to prepare a calibration curve. The molecular weight of the present endothelin converting enzyme was determined in a similar manner. It was found about $5.4 \times 10^5$. The results are depicted in FIG. 2.

(e) Hydrated density

Hydrated density of the endothelin converting enzyme was measured according to an ultracentrifugation method. It was found not greater than about 1.210 g/ml.

(f) Formation of precipitate

To endothelin converting enzyme were added dextran sulfate and manganese chloride to provide final concentrations of 0.65% and 0.2M, respectively. After leaving at room temperature for 6 hours, the precipitate was removed by centrifugation at 2,000 g for 30 min. at 4° C. to collect the supernatant. The endothelin converting activity in the supernatant was determined and found to be not greater than 10% of that of the present endothelin converting enzyme solution before the formation of precipitate. This confirmed that the present endothelin converting enzyme was precipitated by addition of 0.65% dextran sulfate and 0.2M manganese chloride.

(g) Influence of oxidation

An oxidized endothelin converting enzyme of the invention (sample A) was prepared by adding 20 μl of 1 mM aqueous copper sulfate solution to 2 ml of the present endothelin converting enzyme solution (10 mM tris-hydrochloric acid-0.15 M sodium chloride buffer; pH 7.0), dialyzing the mixture in the above buffer (containing 10 μM copper sulfate) saturated with air at room temperature for 18 hours, further dialyzing it in 10 mM tris-hydrochloric acid-0.15M sodium chloride buffer at pH 7.0 at 4° C. for 24 hours and removing copper sulfate. On the other hand, a control sample (sample B) was prepared by dialyzing 2 ml of the present endothelin converting enzyme solution in the above buffer saturated with argon at room temperature for 18 hours, further dialyzing the solution in 10 mM tris-hydrochloric acid-0.15M sodium chloride buffer at pH 7.0 at 4° C. for 24 hours. The endothelin converting activity of samples A and B was determined by the method as described above. The endothelin converting activity of sample A was found not greater than 50% of that of sample B. This confirmed that the present endothelin converting enzyme was inactivated by oxidation.

The invention is further illustrated by the following examples.

EXAMPLE 1

Preparation of endothelin convering enzyme from human blood 20 ml of human blood was coagulated to obtain 8 ml of blood serum. To the serum was added potassium bromide to adjust the density of the serum to about 1.210 g/ml. After adjusting the pH to about 7.0, 7.5 ml of the serum were placed in six centrifuge tubes (3PC tube produced by Hitachi Co., Japan) with each about 1.25 ml portion, and about 1.25 ml each of a solvent (the density being adjusted to about 1.210 g/ml by adding potassium bromide to 0.196M sodium hydrochloride solution) was overlayered. The tube was centrifuged in a RP100AT4 rotor (produced by Hitachi Co.), at 100,000 g and 4° C. for 20 hours. 0.75 ml of the upper layer in each centrifuge tube was collected, placed in a dialysis tube (Spectrum Co., fraction molecular weight of 50,000), and dialyzed overnight using 10 mM tris-hydrochloric acid-0.15M sodium hydrochloride (pH 7.0). After the completion of the dialysis, a sample solution containing the endothelin converting enzyme was concentrated to about 2 ml by embedding the dialysis tube in powdered Sephadex G75 (Pharmacia AB, Uppsala, Sweden). The thus concentrated lipoprotein fraction was subjected to a column of Bio-Gel A-5m (Bio-Rad Laboratories, 1.6 cm φ×90 cm) equilibrated with 10 mM tris-hydrochloric acid-0.15M sodium hydrochloride (pH 7.0), and eluted with the same buffer. A fraction having 126–152 ml of the elution volume was collected to obtain the endothelin converting enzyme. The total activity of the resultant endothelin converting enzyme was found to be 530 U.

EXAMPLE 2

Preparation of human placenta cytoplasmatic fraction

Human placenta (about 5 g) was freed of membrane or the like, well washed with saline, and cut into fine pieces. 20 ml of a 25 mM HEPES-0.2M sucrose buffer (pH 7.4) was added to the placenta pieces and the mixture was homogenized in a Potter-type homogenizer. The resultant homogenate was centrifuged at 1,000 g for 20 minutes and a supernatant was collected by separation. This supernatant was again centrifuged at 10,000 g for 20 minutes and another supernatant was collected by separation. The resultant supernatant was centrifuged at 100,000 g for 2 hours. About 20 ml of a supernatant was recovered as a cytoplasmatic fraction.

EXAMPLE 3

Preparation of endothelin converting enzyme from human placenta

The human placenta cytoplasmatic fraction obtained in Example 2 was subjected to a column of PD-10 (Pharmacia AB) equilibrated with a 0.196M saline and eluted with the same solvent. To the solution was added potassium bromide to adjust the density of the solution to about 1.210 g/ml. After adjusting the pH to about 7.0, 7.5 ml of the solution was placed in six centrifuge tubes (3PC tube produced by Hitachi Co.) with each about 1.25 ml portion and about 1.25 ml each of a solvent (the density being adjusted to about 1.210 g/ml by adding potassium bromide to 0.196M sodium hydrochloride solution) was overlayered. The tube was centrifuged in a RP100AT4 rotor (produced by Hitachi Co.) at 100,000 g and 4° C. for 20 hours. 0.75 ml of the upper layer in each centrifuge tube was collected, placed in a dialysis tube (Spectrum Co., fraction molecular weight of 50,000), and dialyzed overnight using 10 mM tris-hydrochloric acid-0.15M sodium hydrochloride (pH 7.0). After the completion of the dialysis, a sample solution containing the endothelin converting enzyme was concentrated to about 2 ml by embedding the dialysis tube in powdered Sephadex G75 (Pharmacia AB). The sample solution thus concentrated was subjected to a column chromatography of Bio-Gel A-5m (Bio-Rad Laboratories, 1.6 cm φ×90 cm) equilibrated with 10 mM tris-hydrochloric acid-0.15M sodium hydrochloride (pH 7.0) and eluted with the same buffer. A fraction having 126–152 ml of the elution volume was collected to obtain the endothelin converting enzyme. The total activity of the resultant endothelin converting enzyme was found to be 500 U.

EXAMPLE 4

Gel filtration of lipoprotein fraction

Figure 3:
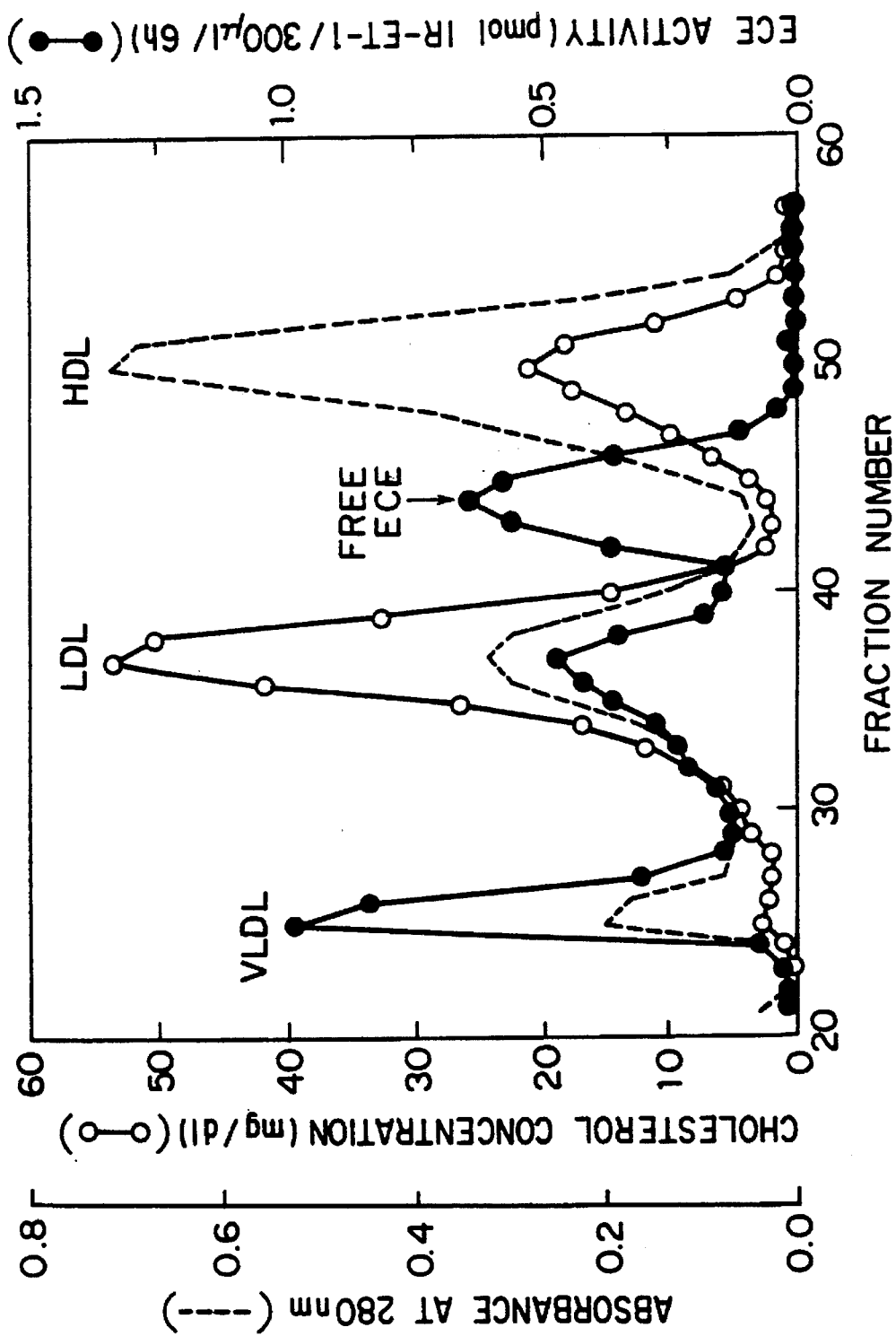
FIG. 3 is a graph showing the test results of endothelin converting enzyme obtained in Example 4.

The lipoprotein fraction (12.8 mg) of human serum origin obtained in Example 1 was subjected to a column (φ 1.6 cm×90 cm) of Bio-Gel A-Sm equilibrated with 10 mM tris-hydrochloric acid-150 mM sodium hydrochloride buffer (pH 7.0) and eluted with the same buffer. Each fraction was measured for absorbance at 280 nm, cholesterol concentration and ECE activity. The results are depicted in FIG. 3, which indicates that the endothelin converting enzyme of the invention is eluted in the position different from each of lipoproteins and no cholesterol is detected in the peak of the present endothelin converting enzyme. From this result, it is concluded that the endothelin converting enzyme of the present invention is a protein different from lipoprotein.

What is claimed is:

1. An isolated, purified human endothelin converting enzyme having the following properties:
   (1) Action: converts big endothelin to endothelin;
   (2) Substrate specificity: acts on big endothelin-1, big endothelin-2, or big endothelin-3;
   (3) Optimum pH: pH 6.5–7.5;
   (4) Molecular weight: about $5.4 \times 10^5$ as measured on gel-filtration using a column of crosslinked agarose gel bead (exclusion limit $5 \times 10^6$ Daltons);
   (5) Inhibitors: inhibited by ethylenediaminetetraacetate (EDTA), phosphoramidon, thiorphan, phenylmethane sulfonyl fluoride (PMSF), and chymostatin;
   (6) Hydrated density: not greater than about 1.210 g/ml;
   (7) Formation of precipitate: precipitation by adding 0.65% dextran sulfate (M.W. 500,000) and 0.2M manganese chloride;
   (8) Influence of oxidation: inactivated by oxidation by copper ion.

2. An endothelin converting enzyme of claim 1 wherein the endothelin converting enzyme is isolated from human blood or human placenta.

\* \* \* \* \*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 38 amino acids
      ( B ) TYPE: amino acid
      ( C ) STRANDEDNESS: Not Relevant
      ( D ) TOPOLOGY: unknown ( i i ) MOLECULE TYPE: peptide ( i x ) FEATURE:
      ( A ) NAME/KEY: Cleavage-site
      ( B ) LOCATION: 21..22

( i x ) FEATURE:
    ( A ) NAME/KEY: Disulfide-bond
    ( B ) LOCATION: 1..15

( i x ) FEATURE:
    ( A ) NAME/KEY: Disulfide-bond
    ( B ) LOCATION: 3..11

( x i ) SEQUENCE DESCRIPTION: SEQ ID NO:1:

```
Cys Ser Cys Ser Ser Leu Met Asp Lys Glu Cys Val Tyr Phe Cys His
 1               5                  10                  15

Leu Asp Ile Ile Trp Val Asn Thr Pro Glu His Val Val Pro Tyr Gly
            20                  25                  30

Leu Gly Ser Pro Arg Ser
            35
```